US008252962B2

(12) United States Patent
Henkelmann et al.

(10) Patent No.: US 8,252,962 B2
(45) Date of Patent: Aug. 28, 2012

(54) METHOD FOR PRODUCING 1,2-PROPANDIOL BY HYDROGENATING GLYCERINE IN A TWO-STEP REACTOR CASCADE

(75) Inventors: Jochem Henkelmann, Mannheim (DE); Roman Prochazka, Mannheim (DE); Oliver Bey, Niederkirchen (DE); Stephan Maurer, Neustadt-Gimmeldingen (DE); Jochen Steiner, Mannheim (DE); Heiko Urtel, Mannheim (DE); Gerhard Theis, Maxdorf (DE); Peter Wahl, Heidelberg (DE); Petra Maier, Mannheim (DE); Georg Mehrl, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 317 days.

(21) Appl. No.: 12/675,900

(22) PCT Filed: Aug. 29, 2008

(86) PCT No.: PCT/EP2008/061385
§ 371 (c)(1),
(2), (4) Date: Mar. 1, 2010

(87) PCT Pub. No.: WO2009/027500
PCT Pub. Date: Mar. 5, 2009

(65) Prior Publication Data
US 2010/0240934 A1    Sep. 23, 2010

(30) Foreign Application Priority Data
Aug. 31, 2007    (EP) ..................................... 07115460

(51) Int. Cl.
C07C 29/60    (2006.01)
(52) U.S. Cl. ....................................................... 568/861
(58) Field of Classification Search .................... 568/861
See application file for complete search history.

(56) References Cited

U.S. PATENT DOCUMENTS

| | | | |
|---|---|---|---|
| 2,360,844 A | | 10/1944 | Bradshaw et al. |
| 4,297,247 A | | 10/1981 | Krabetz et al. |
| 4,476,331 A | * | 10/1984 | Dubeck et al. ............... 568/861 |
| 4,960,960 A | * | 10/1990 | Harrison et al. ............. 568/881 |
| 5,214,219 A | * | 5/1993 | Casale et al. ................ 568/861 |
| 5,254,758 A | * | 10/1993 | Hiles et al. .................. 568/881 |
| 5,354,878 A | | 10/1994 | Connemann et al. |
| 5,395,991 A | * | 3/1995 | Scarlett et al. ............... 568/864 |
| 5,403,962 A | | 4/1995 | Schneider et al. |
| 5,536,694 A | | 7/1996 | Schuetz et al. |
| 5,616,817 A | | 4/1997 | Schuster et al. |
| 5,677,261 A | | 10/1997 | Tenten et al. |
| 6,121,188 A | | 9/2000 | Breitscheidel et al. |
| 6,297,409 B1 | * | 10/2001 | Choque et al. ............... 568/863 |
| 2005/0204612 A1 | | 9/2005 | Connemann et al. |
| 2010/0036175 A1 | | 2/2010 | Franke et al. |
| 2010/0094064 A1 | | 4/2010 | Stankowiak et al. |
| 2010/0179346 A1 | | 7/2010 | Klein et al. |
| 2010/0204527 A1 | * | 8/2010 | Tuck ............................ 568/861 |

FOREIGN PATENT DOCUMENTS

| | | |
|---|---|---|
| CA | 2208720 A1 | 7/1996 |
| CA | 2570915 A1 | 1/2006 |
| CN | 101012149 A | 8/2007 |
| DE | 524101 C | 5/1931 |
| DE | 541362 C | 1/1932 |
| DE | 2628987 A1 | 1/1978 |
| DE | 2909671 A1 | 10/1980 |
| DE | 4021230 A1 | 1/1991 |
| DE | 4028295 A1 | 3/1992 |
| DE | 4302464 A1 | 8/1994 |
| DE | 4335360 A1 | 4/1995 |
| DE | 4345265 A1 | 9/1995 |
| DE | 4446907 A1 | 7/1996 |
| DE | 10218849 A1 | 11/2003 |
| DE | 10243700 A1 | 4/2004 |
| EP | 434062 A1 | 6/1991 |
| EP | 0523015 A2 | 1/1993 |
| EP | 0552463 A1 | 7/1993 |
| EP | 0714700 A2 | 6/1996 |
| EP | 0842699 A2 | 5/1998 |
| GB | 1579159 A | 11/1980 |
| WO | WO-2005/095536 A2 | 10/2005 |
| WO | WO-2006/005505 A1 | 1/2006 |
| WO | WO-2007010299 A1 | 1/2007 |
| WO | WO-2007053705 A2 | 5/2007 |
| WO | WO-2007/099161 A1 | 9/2007 |
| WO | WO-2008/012244 A1 | 1/2008 |
| WO | WO-2008/049470 A1 | 5/2008 |
| WO | WO-2008/089899 A1 | 7/2008 |
| WO | WO-2008/151784 A1 | 12/2008 |

OTHER PUBLICATIONS

U.S. Appl. No. 12/675,873, filed Mar. 1, 2010, Henkelmann et al.
U.S. Appl. No. 12/675,889, filed Mar. 1, 2010, Henkelmann et al.

* cited by examiner

*Primary Examiner* — Brian J Davis
(74) *Attorney, Agent, or Firm* — Connolly Bove Lodge & Hutz LLP

(57) ABSTRACT

The present invention relates to a process for preparing 1,2-propanediol, in which a glycerol-containing stream, especially a stream obtained on the industrial scale in the production of biodiesel, is subjected to a hydrogenation in a two-stage reactor cascade.

20 Claims, 1 Drawing Sheet

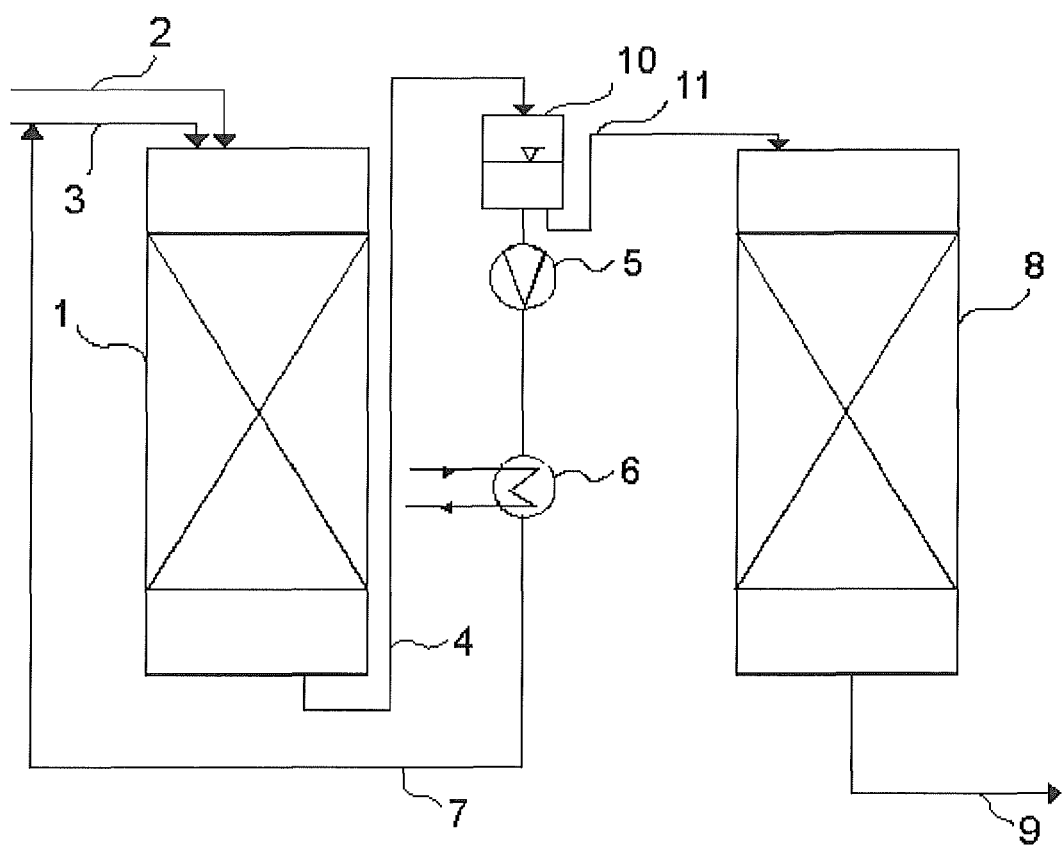

METHOD FOR PRODUCING 1,2-PROPANDIOL BY HYDROGENATING GLYCERINE IN A TWO-STEP REACTOR CASCADE

CROSS-REFERENCE TO RELATED APPLICATIONS

This application is a national stage application (under 35 U.S.C. §371) of PCT/EP2008/061385, filed Aug. 29, 2008, which claims benefit of European application 07115460.3, filed Aug. 31, 2007.

BACKGROUND OF THE INVENTION

The present invention relates to a process for preparing 1,2-propanediol, in which a glycerol-containing stream, especially a stream obtained on the industrial scale in the production of biodiesel, is subjected to a hydrogenation in a two-stage reactor cascade.

Diminishing mineral oil reserves and rising fuel prices are leading to a growing interest in replacing fuels produced on a mineral oil basis with inexpensive alternatives which do not harm the environment. Processes for producing fuels from biogenic fat- or oil-containing starting mixtures and, for example, used oils and animal fats obtained in restaurants have been known for some time, and predominantly rapeseed oil is currently being used as a starting material in the production of biogenic fuels in central Europe. Biogenic oils and fats themselves are less suitable as motor fuel, since they have to be purified beforehand by usually complicated processes. These include removal of lecithins, carbohydrates and proteins, the removal of so-called oil sludge, and the removal of the free fatty acids present in relatively large amounts, for example, in the rapeseed oil. Vegetable oils thus reprocessed nevertheless deviate from the technical properties of conventional diesel fuels in several aspects. For instance, they generally have a higher density than diesel fuel, the cetane number of rapeseed oil is lower than that of diesel fuel, and the viscosity is several times higher compared to that of diesel fuel. This leads to an unacceptable deterioration in the fuel properties, such as to inhomogeneous running performance of the engine, significantly increased noise emission and, as a result of the higher viscosity, poorer atomization and combustion in the combustion chamber. The use of pure vegetable oils therefore leads to carbonization in conventional engines, associated with elevated particle emission. To solve these problems, it is known that the triglycerides present in the biogenic oil and fat starting mixtures (fatty acid esters of glycerol) can be converted to fatty acid monoalkyl esters, especially methyl or ethyl esters. These esters, which are also known as "biodiesel", can generally be used in diesel engines without any great modifications and the emission of uncombusted hydrocarbons and soot particles can in many cases even be reduced compared to normal diesel fuel. In the transesterification of the triglycerides for biodiesel production, glycerol is also obtained (≈10%), which should be sent to a utilization both for reasons of economic viability and of sustainability. There is therefore a need for effective and economically viable processes which also enable utilization of the glycerol obtained in the biodiesel production. These processes should more particularly also be suitable for utilizing further glycerol streams available on the industrial scale.

U.S. Pat. No. 2,360,844 describes a process for producing soaps, in which a crude glyceride is transesterified with $C_1$-$C_4$ alkanols and the glycerol released is removed from the monoalkyl esters. The utilization of the glycerol obtained is not described.

U.S. Pat. No. 5,354,878 describes a process for preparing lower alkyl esters of higher fatty acids with a low residual glycerol content by transesterifying fatty acid triglycerides, and the use of these esters as diesel fuel.

DE 102 43 700 A1 describes an ambient pressure process for preparing alkyl esters of higher fatty acids, especially biodiesel, from fatty acid triglyceride starting mixtures comprising free fatty acids with a combination of acidic esterification and basic transesterification. The glycerol obtained in the transesterification is used partly as an azeotroping agent in the esterification of the free fatty acids.

It is known that polyfunctional alcohols can be converted to low-functionality alcohols by catalytic hydrogenation. For instance, DE-C-524 101 describes such a process in which substances such as glycerol are subjected to a gas phase hydrogenation in the presence of a hydrogenation catalyst with hydrogen in a considerable excess. Specifically, for the hydrogenation of glycerol, Cr-activated copper or cobalt catalysts are used.

DE-C-541 362 describes a process for hydrogenating polyoxy compounds, for example glycerol, in the presence of catalysts at elevated temperatures above 150° C. and under elevated pressure. Specifically, the hydrogenation of glycerol with a nickel catalyst at a temperature of from 200 to 240° C. and a hydrogen pressure of 100 atm is described.

R. Connor and H. Adkins describe, in J. Am. Chem. Soc. 54, 1932, p. 4678-4690, the hydrogenolysis of oxygen-containing organic compounds, including that of 98% glycerol, to 1,2-propanediol in the presence of a copper-chromium-barium oxide catalyst.

C. Montassier et al. describe, in Bulletin de la Société Chimique de France 1989, No. 2, p. 148-155, studies of the reaction mechanism of the catalytic hydrogenation of polyols in the presence of various metallic catalysts, for example of glycerol in the presence of Raney copper.

J. Chaminand et al. describe, in Green Chem. 6, 2004, p. 359-361, the hydrogenation of aqueous glycerol solutions at 180° C. and 80 bar of hydrogen pressure in the presence of supported metal catalysts based on Cu, Pd and Rh.

DE 43 02 464 A1 describes a process for preparing 1,2-propanediol by hydrogenating glycerol in the presence of a heterogeneous catalyst at pressures of from 20 to 300 bar, especially at from 100 to 250 bar, and temperatures from 150° C. to 320° C., wherein glycerol is passed over a catalyst bed in vaporous or liquid form. The catalysts mentioned include copper chromite, copper zinc oxide, copper aluminum oxide, and copper silicon dioxide. The use of glycerol-containing streams from biodiesel production and measures for pretreating such streams before their use for hydrogenation are not described in this document.

EP 0 523 015 describes a process for catalytically hydrogenating glycerol to prepare 1,2-propanediol and 1,2-ethanediol in the presence of a Cu/Zn catalyst at a temperature of at least 200° C. In this process, the glycerol is used as an aqueous solution having a glycerol content of from 20 to 60% by weight; the maximum glycerol content in the working examples is 40% by weight.

WO 2005/095536 describes a low-pressure process for converting glycerol to propylene glycol, in which a glycerol-containing stream having a water content of at most 50% by weight is subjected to a catalytic hydrogenation at a temperature in the range from 150 to 250° C. and a pressure in the range from 1 to 25 bar.

M. A. Dasari et al. describe, in Appl. Catalysis A: General 281, 2005, pages 225-231, a process for low-pressure hydrogenation of glycerol to propylene glycol at a temperature of 200° C. and a hydrogen pressure of 200 psi (13.79 bar) in the presence of a nickel, palladium, platinum, copper or copper chromite catalyst. Different reaction parameters were tested, including the water content of the glycerol used. Although the conversion increased with decreasing water content, the highest selectivity was achieved in this low-pressure process at a water content of 20% by weight.

U.S. Pat. No. 5,616,817 describes a process for preparing 1,2-propanediol by catalytically hydrogenating glycerol at elevated temperature and elevated pressure, in which glycerol having a water content of at most 20% by weight is converted in the presence of a catalyst which comprises from 40% to 70% by weight of cobalt, if appropriate manganese and/or molybdenum and a small content of copper of from 10 to 20% by weight. The temperature is within a range of from about 180 to 270° C. and the pressure within a range of from 100 to 700 bar, preferably from 200 to 325 bar.

The unpublished PCT/EP2007/051983 describes a process for preparing 1,2-propanediol, in which a glycerol-containing stream is subjected to a hydrogenation in the presence of a heterogeneous copper catalyst at a temperature of from 100 to 320° C. and a pressure of from 100 to 325 bar.

BRIEF SUMMARY OF THE INVENTION

It is an object of the present invention to provide an improved process for preparing 1,2-propanediol. For instance, the known processes are still in need of improvement with regard to substantially complete hydrogenation of the glycerol with simultaneously good selectivity based on the desired 1,2-propanediol. In addition, many processes known from the prior art require relatively large amounts of catalyst or have too low a space-time yield. The process provided should more particularly also be suitable for the further processing of glycerol streams obtained on the industrial scale, as obtained in the transesterification of fatty acid triglycerides to prepare alkyl esters of higher fatty acids.

The invention therefore provides a process for preparing 1,2-propanediol, in which
a) a glycerol-containing stream is provided, and
b) the glycerol-containing stream is subjected to a continuous hydrogenation in two hydrogenation reactors connected in series in the presence of a heterogeneous copper catalyst, the conversion in the first reactor being at least 80%, based on the glycerol content.

The hydrogenation product obtained in step b) can, if appropriate, be subjected to at least one workup step (step c)).

A BRIEF DESCRIPTION OF THE FIGURE

FIG. 1 shows the diagram of the two-stage reactor cascade used to perform the hydrogenation process according to example 1.

DETAILED DESCRIPTION OF THE INVENTION

According to the invention, the hydrogenation is effected continuously in two hydrogenation reactors connected in series. Each reactor may have one or more reaction zones within the reactor. The reactors may be identical or different reactors. These may, for example, in each case have identical or different mixing characteristics and/or be divided once or more than once by internals.

Suitable pressure-rated reactors for the hydrogenation are known to those skilled in the art. These include the generally customary reactors for gas-liquid reactions, for example tubular reactors, tube bundle reactors, gas circulation reactors, bubble columns, loop apparatus, stirred tanks (which may also be configured as stirred tank cascades), airlift reactors, etc.

The process according to the invention using heterogeneous catalysts can be performed in fixed bed or suspension mode. The fixed bed method can be performed, for example, in liquid phase mode or in trickle mode. The catalysts are preferably arranged as shaped bodies as described below, for example, in the form of pressed cylinders, tablets, pellets, wagonwheels, rings, stars or extrudates such as solid extrudates, polylobal extrudates, hollow extrudates, honeycombs, etc.

In the suspension mode, heterogeneous catalysts are likewise used. The heterogeneous catalysts are usually used in a finely distributed state and are present finely suspended in the reaction medium.

Suitable heterogeneous catalysts and processes for their preparation are described in detail below.

In the hydrogenation over a fixed bed, at least one reactor is used, in whose interior is arranged a fixed bed through which the reaction medium flows. The fixed bed can be formed from a single bed or from a plurality of beds. Each bed may have one or more zones, at least one of the zones comprising a material active as a hydrogenation catalyst. Each zone may have one or more different catalytically active materials and/or one or more different inert materials. Different zones may each have identical or different compositions. It is also possible to provide a plurality of catalytically active zones which are separated from one another, for example, by inert beds. The individual zones may also have different catalytic activities. To this end, different catalytically active materials can be used and/or an inert material can be added to at least one of the zones. The reaction medium which flows through the fixed bed, in accordance with the invention, comprises at least one liquid phase. The reaction medium may also additionally comprise a gaseous phase.

The reactors used in the hydrogenation in suspension are especially loop apparatus such as jet loops or propeller loops, stirred tanks which may also be configured as stirred tank cascades, bubble columns or airlift reactors.

Preference is given to effecting the continuous hydrogenation in step b) in two fixed bed reactors connected in series. The reactors are preferably operated in parallel flow. The feed streams can be fed in either from the top or from the bottom.

In the hydrogenation, the glycerol and the resulting 1,2-propanediol are preferably present in the liquid phase.

The temperature in the hydrogenation in step b) in both reactors is generally from about 150 to 250° C., especially from 170 to 230° C.

If desired, a different temperature may be established in the second reactor than that in the first reactor. In a specific embodiment, the second reactor is operated with a higher temperature than the first reactor. In addition, the first and/or second reactor may have two or more reaction zones with different temperature. For example, a different temperature, preferably a higher temperature, can be established in a second reaction zone than in the first reaction zone, or a higher temperature than in an upstream reaction zone can be established in each downstream reaction zone, for example, in order to achieve substantially full conversion in the hydrogenation.

The reaction pressure in step b) is preferably, in both reactors, generally from about 30 to 300 bar, more preferably from 60 to 250 bar, especially from 140 to 250 bar.

If desired, a different pressure may be established in the second reactor than that in the first reactor. In a specific embodiment, the second reactor is operated with a higher pressure than the first reactor.

The hydrogen required for the hydrogenation can be fed into the first and, if appropriate, additionally into the second reactor. Preference is given to feeding hydrogen only into the first reactor. The amount of hydrogen fed to the reactors arises from the amount of hydrogen consumed in the hydrogenation reaction and any amount of hydrogen discharged with the offgas. The molar ratio of hydrogen to glycerol is preferably from 1:1 to 500:1, especially from 1.1:1 to 100:1. The hydrogen is preferably used in a stoichiometric excess of from about 2 to 25 mol %, more preferably from 5 to 15 mol %, based on glycerol.

The catalyst hourly space velocity in continuous mode is preferably from 0.05 to 1 kg, more preferably from 0.1 to 0.5 kg, especially from 0.1 to 0.3 kg of glycerol to be hydrogenated per kg (catalyst) per h.

The conversion in the first reactor, based on the glycerol present in the glycerol-containing stream, is preferably at least 85%, more preferably at least 90%, especially at least 92%. The glycerol content converted in the first reactor can be controlled, for example, via the reactor volume and/or the residence time in the first reactor. The total glycerol conversion in step b), based on the glycerol present in the glycerol-containing stream, is preferably at least 97%, more preferably at least 98%, especially at least 99%.

To remove the heat of reaction which arises in the exothermic hydrogenation, it is possible to provide the first and/or the second reactor with at least one cooling apparatus. The heat of reaction can be removed by cooling an external circulation stream or by internal cooling in at least one of the reactors. For the internal cooling, it is possible to use the apparatus customary therefor, generally hollow modules such as Field tubes, tube coils, heat exchanger plates, etc. Alternatively, the reaction can also be effected in a cooled tube bundle reactor.

A two-stage reactor cascade is preferably used for the hydrogenation in step b), wherein the first hydrogenation reactor has a stream from the reaction zone conducted in an external circulation system (external circulation stream, liquid circulation system).

When the reaction mixture hydrogenated in the second reactor has only such low proportions of hydrogenatable glycerol that the exothermicity occurring in the reaction is insufficient to maintain the desired temperature in the reactor, heating of the second reactor (or of individual reaction zones of the second reactor) may also be required. This can be effected analogously to the above-described removal of the heat of reaction by heating an external circulation stream or by internal heating. In a suitable embodiment, the second reactor can be temperature-controlled by using the heat of reaction from the first reactor.

In addition, the heat of reaction withdrawn from the reaction mixture can be used to heat the reactants. For instance, the glycerol feed stream can be mixed at least partly with an external circulation stream and the combined streams can then be conducted into the first reactor. In addition, the glycerol feed stream can be heated with the aid of a heat exchanger which is operated with heat of hydrogenation withdrawn from one of the two reactors.

In a specific embodiment of the process, a reactor cascade composed of two reactors connected in series is used, in which case the reaction is performed adiabatically in the second reactor. In the context of the present invention, this term is used in the technical and not in the physicochemical sense. Thus, the reaction mixture generally experiences a temperature increase as it flows through the second reactor owing to the exothermic hydrogenation reaction. An adiabatic reaction is understood to mean a procedure in which the amount of heat released in the hydrogenation is absorbed by the reaction mixture in the reactor and no cooling by cooling apparatus is employed. The heat of reaction is thus removed from the second reactor with the reaction mixture apart from a residual content which is released from the reactor to the environment as a result of natural heat conduction and heat emission. The second reactor is preferably operated in straight pass.

In one embodiment, additional mixing can be effected in at least one of the reactors used. Additional mixing is advantageous especially when the hydrogenation is effected at high residence times of the reaction mixture. For the mixing, it is possible, for example, to use the streams introduced into the reactors, by introducing them into the particular reactors via suitable mixing apparatus such as nozzles. For the mixing, it is also possible to use streams from the particular reactor conducted in an external circulation system.

To complete the hydrogenation, a discharge which still comprises hydrogenatable glycerol is withdrawn from the first reactor. In a specific embodiment, a discharge is removed from the first reactor and separated into a first and a second substream, in which case the first substream is fed back as a circulation stream to the first reactor, and the second substream is fed to the second reactor. The discharge may comprise dissolved or gaseous fractions of hydrogen. In a specific embodiment, the discharge from the first reactor is fed to a phase separation vessel and separated into a liquid phase and a gaseous phase, the liquid phase is separated into the first and the second substream, and the gas phase is fed separately at least partly to the second reactor. In an alternative embodiment, the discharge from the first reactor is fed to a phase separation vessel and separated into a first liquid hydrogen-depleted substream and a second hydrogen-enriched substream. The first substream is then fed back as a circulation stream to the first reactor, and the second substream is fed to the second reactor (as a glycerol- and hydrogen-containing feed). In a further alternative embodiment, the second reactor is charged with hydrogen not via a hydrogenous feed withdrawn from the first reactor but rather with fresh hydrogen via a separate feed line.

Preference is given to an embodiment of process step b), in which b1) a glycerol-containing feed and hydrogen are fed into the first reactor of a reaction system which consists of one reactor with a stream conducted in an external circulation system (circulation reactor) and a downstream reactor operated in straight pass (adiabatic flow tube reactor), and converted up to a partial conversion in the presence of a heterogeneous copper catalyst, b2) a discharge which comprises hydrogen, glycerol and 1,2-propanediol is withdrawn from the first reactor, b3) the discharge is separated into a first liquid hydrogen-depleted substream and a second hydrogen-enriched substream, b4) the first substream, after withdrawal of some of the heat contained, is recycled into the first reactor, b5) the second substream is fed into the second reactor and converted further in the presence of a heterogeneous copper catalyst.

The above-described process variant is suitable particularly advantageously for controlling the reaction temperature and the heat transfer between reaction medium, delimiting apparatus walls and environment. A further means of controlling the heat balance consists in regulating the inlet temperature of the glycerol-containing feed. For instance, a lower temperature of the entering feed generally leads to improved removal of the heat of hydrogenation. When the catalyst activity declines, the inlet temperature can be selected at a higher level in order to achieve a higher reaction rate and thus to compensate the declining catalyst activity. Advantageously, the lifetime of the catalyst used can generally be prolonged in this way.

The first substream is generally recycled chemically unchanged into the reaction system. If desired, the temperature and/or the pressure before the recycling can be adjusted to the desired values. The first substream can be fed into the first reactor together with the glycerol-containing feed or separately therefrom. The weight ratio of first substream fed into the first reactor to fresh glycerol-containing feed is preferably within a range of from 1:1 to 50:1, more preferably from 2:1 to 30:1.

In a specific embodiment, heat is also withdrawn from the second substream before entry into the second reactor. To this end, a customary heat exchanger can be used, which enables the reuse of the amount of energy obtained at another point in the process, for example in the separation of the reaction discharge from the second reactor.

FIG. 1 shows the diagram of a two-stage reactor cascade suitable for performing the hydrogenation process, omitting the reproduction of details which are not relevant for the illustration of the invention for reasons of clarity. The plant comprises a first hydrogenation reactor (1) and a second hydrogenation reactor (8). The hydrogenation reactor (1) is designed as a circulation reactor, and the hydrogenation reactor (8) as an adiabatic flow tube reactor. Hydrogen gas is introduced under pressure into the reactor (1) via the pipeline (2). A glycerol-containing stream is introduced into the reactor (1) via the pipeline (3). A discharge is withdrawn from the reactor (1) via the pipeline (4) and the pump (5) and fed to the phase separation vessel (10). The liquid phase obtained in the phase separation vessel (10) is cooled in the heat exchanger (6) and, as a circulation stream (7), fed back to the reactor (1). The phase separation vessel (10) may, as shown, be designed separately or alternatively integrated into reactor (1). In the phase separation vessel (10), a further stream (11) which comprises gaseous and liquid fractions is removed and fed via the separate line (11) to the reactor (8). In a further alternative embodiment, the reactor (8) is charged with hydrogen not via a feed withdrawn from the reactor (1) but rather with fresh hydrogen via a separate feed line. The hydrogenation product leaves reactor (8) via the pipeline (9).

Suitable glycerol-containing streams for use in the process according to the invention are in principle all glycerol-containing streams, even those from industrially practised processes and with the purity levels which occur there. These include especially glycerol-containing streams from the processing of oil- and/or fat-containing starting materials, for example, from soap production, fatty acid and fatty acid ester production, etc. The glycerol-containing stream provided in step a) is preferably a glycerol-containing stream which is obtained in the preparation of alkyl esters of higher fatty acids by transesterification of fatty acid triglycerides as obtained especially in the production of biodiesel. This embodiment of the process according to the invention is described in detail hereinafter.

The glycerol-containing stream used in step a) preferably has a water content of at most 30% by weight, preferably of at most 20% by weight. Particular preference is given to a water content corresponding to glyceryl monohydrate (water content 16.3% by weight) or less. In a specific embodiment, a glycerol-containing stream which is essentially anhydrous is used. In the context of the present invention, "essentially anhydrous" is understood to mean a water content of at most 3% by weight, more preferably of at most 1% by weight. The use of glycerol-containing streams having a water content in the range up to 30% by weight, especially up to 20% by weight, enables the preparation of 1,2-propanediol with high yields and with high selectivity within the temperature and pressure range used for the hydrogenation. The hydrogenation of glycerol-containing streams, which are not essentially anhydrous and especially of streams which have a higher water content than glyceryl monohydrate is likewise possible with high yields and selectivities, but less economically viable owing to the reduced space-time yields. Nevertheless, a water content in the range from 3 to 30% by weight may be advantageous for the rheological properties during the hydrogenation. A specific embodiment of the process according to the invention therefore relates to the use of glycerol-containing streams having a water content of from 3 to 30% by weight, preferably from 5 to 20% by weight, for reducing the viscosity in the hydrogenation.

The glycerol-containing streams may, instead of or in addition to water, comprise at least one further, preferably glycerol-miscible (and hence generally also water-miscible), organic solvent. The glycerol-containing streams provided in step a) preferably have a total solvent content of at most 20% by weight, more preferably at most 15% by weight, more particularly at most 10% by weight and especially at most 5% by weight. When solvent mixtures which comprise water and at least one glycerol- and/or water-miscible organic solvent are used, the proportion of the organic solvent is preferably at most 50% by weight, more preferably at most 20% by weight, based on the total weight of the solvent. Suitable glycerol-miscible organic solvents are $C_1$-$C_4$ alkanols, such as methanol, ethanol, n-propanol, isopropanol, n-butanol, tert-butanol, polyols and mono- and dialkyl ethers thereof, cyclic ethers, such as dioxane and tetrahydrofuran, etc. Suitable solvents are also aromatic hydrocarbons such as benzene, toluene, or the xylenes. Preferred organic solvents are $C_1$-$C_4$ alkanols, especially methanol and/or ethanol and mixtures thereof with water. However, the glycerol-containing streams used in step a) preferably do not have any organic solvent.

The glycerol-containing streams provided in step a) may be subjected to at least one workup step. This includes, for example, at least one purification step for removing undesired components. This also includes a reduction in the content of water and/or if present, of organic solvent.

According to the origin, the glycerol-containing streams may also comprise inorganic salts as an undesired component. These can be removed from the crude glycerol by the workup processes described below. A suitable process for this purpose is especially a thermal workup (for example using a Sambay evaporator).

According to the origin, the glycerol-containing streams may also comprise catalyst poisons, i.e. components which impair the hydrogenation by deactivating the hydrogenation catalyst. These include, for example, nitrogen compounds such as amines, and sulfur compounds such as sulfuric acid, hydrogen sulfide, thioalcohols, thioethers, e.g. dimethyl sulfide and dimethyl disulfide, carbon oxide sulfide, amino acids, e.g. amino acids comprising sulfur groups and additional nitrogen groups, fatty acids and salts thereof, etc. The catalyst poisons also include halogen compounds, traces of customary extractants, for example, acetonitrile or N-methylpyrrolidone, etc., and in some cases organic phosphorus and arsenic compounds. A catalyst poison frequently present in glycerol-containing streams from oil and fat processing is sulfuric acid, which is used as a catalyst in the esterification or transesterification.

For the workup of the glycerol-containing streams in step a), it is possible, for example, to use a thermal workup, preferably a distillation, an adsorption, an ion exchange, a membrane separation process, a crystallization, an extraction or a combination of two or more of these processes. Membrane separation processes using membranes of defined pore sizes are suitable especially for reducing the water content and/or for removing salt. Crystallization is also understood to mean the partial freezing of the glycerol-containing streams at cooled surfaces. It is thus possible to remove impurities which are accumulated in the solid phase.

In a first embodiment, the glycerol-containing stream is subjected in step a) to a distillation to reduce the water content and/or to remove components which impair the catalytic hydrogenation. This can in principle be done by customary distillation processes known to those skilled in the art. Suitable apparatus for distillative workup comprises distillation columns, such as tray columns which may be equipped with bubble-caps, sieve plates, sieve trays, structured packings, random packings, valves, side draws, etc., evaporators such as thin-film evaporators, falling-film evaporators, forced-circulation evaporators, Sambay evaporators, etc., and combinations thereof. The removal of sulfuric acid is possible merely by a simple distillation, especially a short-path distillation.

Suitable separation processes are described in the documents which follow: Sattler, Klaus: Thermische Trennverfahren [Thermal Separation Processes], 3rd edition, Wiley VCH, 2001; Schlünder E. U., Thurner F.: Destillation, Absorption, Extraktion [Distillation, Absorption, Extraction], Springer Verlag, 1995; Mersmann, Alfons: Thermische Verfahrenstechnik [Thermal Process Technology], Springer Verlag, 1980; Grassmann P., Widmer F.: Einführung in die thermische Verfahrenstechnik [Introduction to Thermal Process Technology], de Gruyter, 1997; Weiss S., Militzer K.-E., Gramlich K.: Thermische Verfahrenstechnik, Dt. Verlag für Grundstoffindustrie, Leipzig, Stuttgart, 1993. Reference is made here to these documents.

In a further embodiment, the glycerol-containing stream is subjected in step a) to a catalytic desulfurization, if appropriate in the presence of hydrogen, to reduce the content of sulfur compounds, especially aromatic sulfur compounds. Suitable desulfurizing agents comprise a metal component, the metal preferably being selected from the metals of groups 6, 7, 8, 9, 10, 11 and 12 of the Periodic Table. The metals are preferably selected from Mo, Ni, Cu, Ag, Zn and combinations thereof. Suitable further components of the desulfurizing agents are dopants. The metal component may be used in oxidic form, reduced form or in the form of a mixture which comprises oxidized and reduced components. The active component of the desulfurizing agent (metal component(s) and if appropriate, dopant(s)) may be applied to a support. Suitable supports are in principle the adsorbents and catalyst supports specified below. The support material is preferably selected from activated carbon, graphite, carbon black, $Al_2O_3$, $SiO_2$, $TiO_2$, $ZrO_2$, SiC, silicates, zeolites, aluminas (e.g. bentonites) and combinations thereof. The application of at least one metal component and if appropriate of further components to a support material can be effected by known processes, for example by (co)-precipitation or impregnation. The desulfurizing agents may be used as shaped bodies, for example, in the form of pressed cylinders, tablets, pellets, wagonwheels, rings, stars or extrudates, such as solid extrudates, polylobal extrudates, hollow extrudates and honeycombs, or other geometric bodies. Unsupported desulfurizing agents can be shaped by customary processes, for example by extrusion, tableting, etc. The shape of supported desulfurizing agents is determined by the shape of the support.

For the catalytic desulfurization, preference is given to using a desulfurizing agent which comprises copper and zinc in an atomic ratio of from 1:0.3 to 1:10, preferably from 1:0.5 to 1:3, especially from 1:0.7 to 1:1.5. Preference is given to using a desulfurizing agent which comprises from 35 to 45% by weight of copper oxide, from 35 to 45% by weight of zinc oxide and from 10 to 30% by weight of aluminum oxide. In a specific embodiment, the desulfurizing agent is a component capable of being used as a dehydrogenation catalyst in step b). In this regard, reference is made to the disclosure which follows regarding hydrogenation catalysts of the aforementioned composition and processes for their preparation.

In one embodiment of this process variant, the glycerol-containing streams are contacted with the desulfurizing agent in at least one desulfurization zone and then hydrogenated in at least one reaction zone.

It is obvious to the person skilled in the art that the specific configuration and arrangement of the desulfurization and reaction zone(s) can be effected in any known manner. It is possible to arrange the desulfurization and reaction zone(s) spatially separately from one another, i.e. to separate them from one another in construction terms by virtue of the apparatus arrangement or else to realize them in one or more combined desulfurization/hydrogenation zone(s).

The copper-zinc desulfurizing agent can be obtained, for example, by a customary precipitation or coprecipitation process and be used in oxidized or in reduced form.

In a particular embodiment, the copper-zinc desulfurizing agent comprises at least copper, zinc and aluminum, in which case the copper:zinc:aluminum atomic ratio is in the range from 1:0.3:0.05 to 1:10:2, preferably from 1:0.6:0.3 to 1:3:1 and especially from 1:0.7:0.5 to 1:1.5:0.9.

For conversion to the reduced form it is possible to subject the desulfurizing agent to a hydrogen reduction. This is performed at from about 150 to 350° C., preferably at from about 150 to 250° C., in the presence of hydrogen, in which case the hydrogen is diluted by an inert gas, for example nitrogen, argon, methane, especially nitrogen, such that the hydrogen content is 10% by volume or less, preferably 6% by volume or less, especially from 0.5 to 4% by volume. The copper-zinc desulfurizing agent thus obtained ("reduced form") may be used in this form in the desulfurization.

In one embodiment, the desulfurization of the glycerol-containing stream is performed over the copper-zinc desulfurizing agent in oxidized form without addition of hydrogen.

In a further embodiment, the desulfurization of the glycerol-containing stream is performed over the copper-zinc desulfurizing agent in oxidized form in the presence of hydrogen.

In a further embodiment, the desulfurization of the glycerol-containing stream is performed over the copper-zinc desulfurizing agent in reduced form without addition of hydrogen.

In a further embodiment, the desulfurization of the glycerol-containing stream is performed over the copper-zinc desulfurizing agent in reduced form in the presence of hydrogen.

Typically, the desulfurization is performed within a temperature range from 40 to 200° C., particularly at from 50 to 180° C., especially at from 60 to 160° C., preferably at from 70 to 120° C., at a pressure of from 1 to 40 bar, particularly at from 1 to 32 bar, preferably at from 1.5 to 5 bar, especially at from 2.0 to 4.5 bar. The desulfurization can be performed in the presence of inert gases, for example nitrogen, argon or methane. In general, however, the desulfurization is performed without addition of inert gases.

Typically—if desired—hydrogen is used here with a purity of $\geq 99.8\%$ by volume, especially of $\geq 99.9\%$ by volume, preferably of $\geq 99.95\%$ by volume. These purities apply analogously to the hydrogen, which is used in the optionally performed activations of the catalysts.

Typically, the weight ratio of the glycerol-containing stream to hydrogen is in the range from 40 000:1 to 1000:1, particularly in the range from 38 000:1 to 5000:1, more particularly in the range from 37 000:1 to 15 000:1, preferably in the range from 36 000:1 to 25 000:1, especially in the range from 35 000:1 to 30 000:1.

The glycerol-containing stream thus desulfurized generally has a content of sulfur impurities, especially of aromatic sulfur compounds, of at most 70 ppb, preferably of at most 50 ppb, and the total sulfur content is a total of $\leq 200$ ppb, preferably $\leq 150$ ppb, especially $\leq 100$ ppb.

The above-described desulfurizing agents also enable the reduction in the level of or the removal of chlorine, arsenic and/or phosphorus or corresponding chlorine, arsenic and/or phosphorus compounds from the aromatic hydrocarbon or the mixture of aromatic hydrocarbons.

In a further embodiment, the glycerol-containing stream is contacted in step a) with at least one adsorbent to remove components which impair the catalytic hydrogenation.

The adsorbents preferably have a specific surface area, determined according to BET, in the range from 10 to 2000 $m^2/g$, more preferably in the range from 10 to 1500 $m^2/g$, more particularly in the range from 10 to 400 $m^2/g$, especially in the range from 60 to 250 $m^2/g$.

Suitable adsorbents are, for example, active aluminum oxides. They are prepared, for example, proceeding from aluminum hydroxide, which is obtainable by customary precipitation processes from aluminum salt solutions. Active aluminum oxides suitable for the process according to the invention are also obtainable proceeding from aluminum hydroxide gels. To prepare such gels, it is possible, for example, to activate precipitated aluminum hydroxide by customary workup steps, such as filtering, washing and drying, and then if appropriate to grind or agglomerate it. If desired, the resulting aluminum oxide can then also be subjected to a shaping process, such as extrusion, granulation, tableting, etc. Suitable adsorbents are preferably the Selexsorb™ types from Alcoa.

Suitable adsorbents are also aluminum oxide-containing solids. These include, for example, the aluminas which likewise comprise aluminum oxides as the main constituent.

Additionally suitable adsorbents are aluminum phosphates.

Further suitable adsorbents are silicon dioxides, which are obtainable, for example, by dewatering and activating silica gels. A further process for preparing silicon dioxide is the flame hydrolysis of silicon tetrachloride, in which suitable variations of the reaction parameters, for example of the stoichiometric composition of the reactant mixture and of the temperature, allow the desired surface properties of the resulting silicon dioxide to be varied within wide ranges.

Further suitable adsorbents are kieselguhrs, which likewise have silicon dioxides as the main constituent. These include, for example, the diatomaceous earths obtained from silica sediments.

Further suitable adsorbents are titanium dioxides and zirconium dioxides, as described, for example, in Römpp, Chemie-Lexikon, 9th ed. (paperback), vol. 6, p. 4629 ff. and p. 5156 ff. and the literature cited there. This is fully incorporated here by reference.

Further suitable adsorbents are phosphates, especially condensed phosphates, for example, fused or calcined phosphates which have a large active surface area. Suitable phosphates are described, for example, in Römpp, Chemie-Lexikon, 9th ed. (paperback), vol. 4, p. 3376 ff. and the literature cited there. This is fully incorporated here by reference.

Further suitable adsorbents are carbon-containing adsorbents, preferably activated carbon. Activated carbon is understood here generally to mean carbon with a porous structure and high internal surface area. To prepare activated carbon, vegetable, animal and/or mineral carbon-containing raw materials are heated, for example, with dehydrating agents, such as zinc chloride or phosphoric acid, or carbonized by dry distillation and then activated oxidatively. For this purpose, the carbonized material can, for example, be treated with steam, carbon dioxide, and/or mixtures thereof at elevated temperatures of from about 700 to 1000° C.

It is also possible to use ion exchangers and/or adsorber resins.

The adsorbents are preferably selected from titanium dioxides, zirconium dioxides, silicon dioxides, kieselguhr, aluminum oxides, aluminum oxide-containing solids, aluminum phosphates, natural and synthetic aluminum silicates, phosphates, carbon-containing adsorbents and mixtures thereof.

The adsorbents generally have a specific surface area, determined according to BET, in the range from about 10 to 2000 $m^2/g$, more particularly in the range from 10 to 1500 $m^2/g$ and especially in the range from 20 to 600 $m^2/g$.

For the adsorptive removal of undesired components, more particularly of components which impair the catalytic hydrogenation, the glycerol-containing stream is contacted in step a) with at least one adsorbent in an adsorption zone.

In a specific embodiment, an adsorbent which comprises at least one component also capable of being used as a hydrogenation catalyst in step b) is used. Full reference is made here to the hydrogenation catalysts described in detail below. Also suitable for use as adsorbents are combinations of two or more than two adsorbents. It is possible to use exclusively components capable as hydrogenation catalysts, exclusively adsorbents not suitable as hydrogenation catalysts, and combinations thereof.

In a preferred embodiment, the adsorbent and the hydrogenation catalyst used are the same component. If appropriate, one or more further conventional adsorbents other than the hydrogenation catalyst, as described above, are additionally used here.

In one configuration of the process, the glycerol-containing streams are contacted with the adsorbent in at least one adsorption zone and then hydrogenated in at least one reaction zone.

It is obvious to the person skilled in the art that the specific configuration and arrangement of the adsorption and reaction zone(s) can be effected in any known manner. Preference is given to arranging the adsorption and reaction zone(s) spatially separately from one another, i.e. to separating them from one another in construction terms by virtue of the apparatus configuration.

When different adsorbents are used, it is possible, for example, to provide a first adsorption zone in a first reactor which comprises a first adsorbent, and separately, i.e. separately therefrom in apparatus terms, for example in a second reactor, to provide a second adsorption zone which comprises a second adsorbent. In this case, the first and/or the second adsorbent may comprise at least one component capable of being used as a hydrogenation catalyst.

In a further embodiment, a conventional adsorbent is used together with an adsorbent capable of hydrogenation in a single adsorption zone, for example in layered form one on top of another, mixed in the form of a random distribution or in the form of a gradient bed. The use in mixed form allows, in some cases, better control of the temperature. In the case of a gradient bed, it is possible to use linear and nonlinear gradients. It may be advantageous here to undertake the distribution within the bed such that the glycerol-containing stream to be hydrogenated is first contacted with the conventional adsorbent before it is contacted with the adsorbent capable of hydrogenation.

Advantageously, at least two adsorption zones will be arranged such that the glycerol-containing stream to be hydrogenated is contacted with a conventional adsorbent in the first adsorption zone, and is contacted with an adsorbent which comprises at least one component capable of being used as a hydrogenation catalyst in the second adsorption zone.

The glycerol-containing streams provided in step a) of the process according to the invention stem preferably from the production of biodiesel. In the context of the present invention "biodiesel" is understood to mean a mixture of fatty acid monoalkyl esters which can be obtained from biogenic oil- and/or fat-containing starting mixtures and can be used as fuel in diesel engines.

Suitable starting mixtures for providing the glycerol-containing stream are in principle all available biogenic oil- and/or fat-containing starting mixtures. Oils and fats are generally solid, semisolid or liquid fatty acid triglycerides, especially from vegetable and animal sources, which, in chemical terms, essentially consist of glyceryl esters of higher fatty acids. Suitable higher fatty acids are saturated or mono- or polyunsaturated fatty acids having preferably from 8 to 40, more preferably from 12 to 30, carbon atoms. These include, for example, n-nonanoic acid, n-decanoic acid, n-undecanoic acid, n-tridecanoic acid, myristic acid, pentadecanoic acid, palmitic acid, margaric acid, nonadecanoic acid, arachic acid, behenic acid, lignoceric acid, cerotic acid, melissic acid, palmitoleic acid, oleic acid, linoleic acid, linolenic acid, stearic acid, eleostearic acid, etc.

Vegetable fats and oils are based essentially on fatty acids with an even carbon atom number, whereas animal fats and oils may also comprise fatty acids having an odd carbon atom number in free form or in bound foam as triglyceride esters. The unsaturated fatty acids which occur in vegetable fats and oils are present in the cis form, while animal fatty acids frequently have trans-configuration.

To provide the glycerol-containing stream in step a), it is possible in principle to employ used or unused, unpurified or purified vegetable, animal or technical oils or fats or mixtures thereof. These may comprise portions of further ingredients, for example free fatty acids. The proportion of free fatty acids is generally from 0% to 50%, for example from 0.1 to 20%, of the starting mixture used for the transesterification of the fatty acid triglycerides. Free fatty acids may, if desired, be removed before or after the transesterification of the fatty acid triglycerides. Salts of these fatty acids (e.g. the alkali metal salts) may be converted beforehand to the free acid by acidification with a strong acid, e.g. HCl. The free fatty acids are removed, for example, by centrifugation. The free fatty acids present in the starting mixture are preferably likewise converted to the alkyl esters. This can be done before, during or after the transesterification of the fatty acid triglycerides.

Used fats and oils suitable for providing the glycerol-containing stream in step a) are fat- and/or oil-containing components which, after they have been obtained from appropriate biogenic starting materials, have first been used for other purposes, for example for industrial purposes or purposes of food preparation, and which, owing to this use, are chemically modified or unmodified or may have additional constituents, which are especially connected to this use. These may, if desired, be removed at least partly by transesterification before use for providing the glycerol-containing stream. Unused fats and oils suitable for providing the glycerol-containing stream in step a) are fat- or oil-containing components which, after they have been obtained from the appropriate vegetable or animal starting materials, have not yet been set to any other use and which therefore have only constituents which stem from the starting materials or are connected to the recovery from the starting materials. It is also possible for constituents other than fatty acid triglycerides (and if appropriate, free fatty acids), if desired, to be removed at least partly from these starting materials by transesterification before use for providing the glycerol-containing stream.

For purification and/or enrichment, the unused or used fats or oils can be subjected to a removal of undesired constituents, such as lecithins, carbohydrates, proteins, oil sludge, water, etc.

Vegetable oils and fats are those which stem predominantly from vegetable starting materials such as seeds, roots, leaves or other suitable plant parts. Animal fats or oils stem predominantly from animal starting materials, such as animal organs, tissues or other body parts or body fluids such as milk. Technical oils and fats are those which are obtained especially from animal or vegetable starting materials and are processed for technical purposes. The used or unused, unpurified or purified oils and/or fats used in accordance with the invention are especially selected from the group consisting of soapstock, brown grease, yellow grease, technical tallow, technical lard, deep fat fryer oils, animal fat, edible tallow, vegetable crude oils, animal crude oils or fats, or mixtures thereof.

"Soapstock" is understood to mean a by-product obtained in the processing of vegetable oils, especially a by-product from cooking oil refineries based on soybean oil, colza oil or sunflower oil. Soapstock has a proportion of free fatty acids of from about 50% to 80%.

"Brown grease" is understood to mean an animal fat-containing waste product which has a proportion of free fatty acids from more than 15% to 40%. "Yellow grease" comprises from about 5% to 15% free fatty acids.

"Technical tallow" and "technical lard" are understood to mean animal fats which are produced for technical purposes and are obtained by the dry or wet melting processes, for example, from slaughter waste. Technical tallows are rated and traded according to their acid number, the content of free fatty acids, according to the origin, being, for example between 1 and 20% by weight, such as in the range from 1 to 15% by weight. However, the content of free fatty acids may be even more than 20% by weight.

The "animal fats" include especially fat-containing waste products occurring in the utilization of poultry, cattle, pig, fish and marine mammal bodies, for example, solar stearine, a solid residue which remains after the extractive pressing of lard oil from porcine lard.

The glycerol-containing stream is provided in step a) preferably from vegetable crude oils as the starting material. It is possible to proceed from unpurified vegetable crude oils, i.e. from liquid or solid compositions which are obtained from vegetable starting materials, for example, by pressing, and have not experienced any other treatment than settling within generally customary periods and centrifugation or filtering, in which only mechanical forces such as gravity, centrifugal force or pressure are used to separate the oil from solid constituents. Such unpurified vegetable crude oils may also be vegetable oils obtained by extraction when their properties differ only insignificantly, if at all, from the corresponding vegetable oils obtained by means of pressing. The proportion of free fatty acids in unpurified vegetable fats and oils is different and is, for example, from about 0 to 20%, for example from 0.1 to 15%.

It will be appreciated that the vegetable oils, before being used for transesterification, may be subjected to one or more workup steps, as described in more detail below. For instance it is also possible to use purified vegetable oils, for example raffinates or semi-raffinates, of the aforementioned vegetable oils as starting materials.

For the provision of the glycerol-containing stream in step a), preference is given to using a vegetable oil or fat which is preferably selected from rapeseed oil, palm oil, colza oil, soybean oil, sunflower oil, maize kernel oil, cottonseed oil, palm kernel and coconut fat, and mixtures thereof. Particular preference is given to using rapeseed oil or a rapeseed oil-containing mixture.

Also suitable for providing the glycerol-containing stream in step a) is animal oil or fat, which is preferably selected from milk fat, wool fat, bovine tallow, porcine lard, fish oils, train oil, etc. and mixtures thereof. These animal fats or oils too may, before they are used for transesterification, be subjected to one or more workup steps as described in more detail below.

The provision of the glycerol-containing stream in step a) preferably comprises the following steps:

a1) providing a biogenic fat- and/or oil-containing starting mixture,
a2) transesterifying the fatty acid triglycerides present in the starting mixture with at least one $C_1$-$C_9$ monoalcohol and if appropriate esterifying the free fatty acids present in the starting mixture to form an esterification mixture,
a3) separating the esterification mixture to obtain at least one fraction enriched in biodiesel and at least one fraction enriched in glycerol released in the transesterification,
a4) if appropriate, purifying the glycerol-enriched fraction.

Step a1)

In a preferred embodiment, the provision of the biogenic fat- and/or oil-containing starting mixture in step a1) comprises at least one purification step. For purification, the fat- and/or oil-containing starting mixture can be subjected to at least one customarily used purification process for fats and oils, such as clarification, filtration, treatment with bleaching earths or treatment with acids or alkali to remove troublesome impurities such as proteins, phosphatides and sludges, and a combination of at least two of these purification steps.

Step a2)

For the transesterification of the fatty acid triglycerides, preference is given to using at least one $C_1$-$C_9$ monoalcohol, especially at least one $C_1$-$C_4$ monoalcohol. Preference is given to the use of methanol or ethanol.

The fatty acid triglycerides can be transesterified under acidic or preferably basic catalysis. Suitable acids are, for example, mineral acids such as HCl, $H_2SO_4$ or $H_3PO_4$.

The catalyst used is preferably at least one base. This is preferably selected from alkali metal hydroxides, such as NaOH and KOH, alkaline earth metal hydroxides, such as $Ca(OH)_2$, alkali metal and alkaline earth metal $C_1$-$C_6$ alkoxides such as $NaOCH_3$, $KOCH_3$, $Na(OCH_2CH_2)$ and $Ca(OCH_2CH_2)_2$ and mixtures thereof. Particular preference is given to using NaOH, KOH or $NaOCH_3$, very particular preference to $NaOCH_3$.

The amount of the base used is typically within the range from 0.1 to 10% by weight, especially from 0.2 to 5% by weight, based on the amount of fatty acid triglycerides used.

The base is preferably used in the form of an aqueous or alcoholic, more preferably alcoholic, solution. Advantageously, the solvent used for the base is the solvent already used for alcoholysis of the triglycerides. Preference is given to using a $NaOCH_3$ solution in methanol for the transesterification.

The transesterification is effected preferably at a temperature of from about 20 to 150° C., especially from 30 to 95° C.

The transesterification is effected in apparatus which is known to those skilled in the art and is customary therefor. In a suitable embodiment, the transesterification is effected continuously. Preference is given to effecting the transesterification in at least one column, in which case the resulting transesterification mixture is simultaneously subjected to a separation. In general, a relatively high boiling phase enriched in the basic catalyst, in unconverted monoalcohol and in glycerol formed in the transesterification, and a relatively low boiling phase enriched in the transesterification product are obtained. When the transesterification product still comprises as yet untransesterified triglycerides, they may likewise be removed and subjected to another transesterification in the first or a further transesterification stage.

Subsequently, the last transesterification mixture is transferred to a drying unit, which once again removes residual amounts of water. After the drying in the drying apparatus, the desired biodiesel end product is present in purified form and can be used directly as a fuel.

When the fat- and/or oil-containing starting mixture used to provide the glycerol-containing stream in step a) comprises free fatty acids, they can preferably be subjected to an esterification for conversion to esters, suitable for biodiesel.

The free fatty acids are preferably transesterified with the same $C_1$-$C_9$ monoalcohol which has been used for the transesterification of the fatty acid triglycerides. The free fatty acids can be esterified before, during or after the transesterification of the fatty acid triglycerides. In a preferred embodiment, the free fatty acids are esterified before the transesterification of the fatty acid triglycerides.

The free fatty acids can be esterified under basic or preferably acidic catalysis. Suitable acids are the aforementioned mineral acids such as HCl, $H_2SO_4$ or $H_3PO_4$, p-toluenesulfonic acid, etc. The esterification is effected preferably at a temperature of from about 20 to 95° C., especially from 40 to 80° C.

The esterification is effected in apparatus which are known to those skilled in the art and are customary therefor. This includes stirred tanks and/or columns which, if desired, are connected to form cascades. Preference is given to esterifying the free fatty acids in at least one esterification unit designed as a column, in which case the resulting esterification mixture is simultaneously subjected to a separation. In a suitable embodiment, the esterification is effected in the presence of an entrainer for facilitating the separation.

Step a3)

During or after the transesterification and/or esterification, the esterification mixture is subjected to a separation to obtain at least one fraction enriched in $C_1$-$C_9$ monoalkyl esters and at least one fraction enriched in glycerol released in the course of transesterification. The separation is preferably effected by distillation by customary processes known to those skilled in the art. Suitable distillation apparatus is that mentioned above.

Step a4)

The glycerol-enriched fraction obtained after separation of the esterification mixture in step a3) can, if appropriate, be subjected to at least one workup step. This includes, for example, the removal of undesired components such as salts, and of components which impair the catalytic hydrogenation or the removal of water and, if present, organic solvent. Full reference is made to the above remarks regarding these workup steps.

The heterogeneous hydrogenation catalysts used in the process according to the invention may be unsupported catalysts or supported catalysts. They may be used in the form of catalysts of homogeneous composition, impregnated catalysts, coated catalysts and precipitated catalysts.

In principle, a multitude of copper catalysts are suitable, which may additionally comprise at least one further element of main group I, II, III, IV or V, of transition group I, II, IV, V, VI, VII or VIII and of the lanthanides (IUPAC: Groups 1 to 15 and the lanthanides), especially Ca, Mg, Al, La, Ti, Zr, Cr, Mo, W, Mn, Ni, Co, Zn and combinations thereof.

A specific embodiment of catalysts which are suitable particularly advantageously for use in the process according to the invention is that of skeletal or metal sponge catalysts, which are referred to as "Raney catalysts". These include especially Raney copper and copper-containing metal alloys in the form of a Raney catalyst. Preference is given to Raney catalysts whose metal component consists of copper to an extent of at least 95%, especially to an extent of 99%. Processes for preparing Raney catalysts are known to those skilled in the art and are described, for example, in DE-A-43 35 360, DE-A-43 45 265, DE-A-44 46 907 and EP-A-842 699. Raney copper can be prepared in a manner known per se by treating copper-aluminum alloys with alkali metal hydroxides. A Raney catalyst suitable for use in the process according to the invention is, for example, obtainable by preparing a mixture of at least one copper-containing catalyst alloy and at least one binder, said catalyst alloy comprising copper and if appropriate at least one further catalytically active catalyst metal and a leachable alloy component, if appropriate with addition of moistening agents and/or additives such as deformation assistants, lubricants, plasticizers and/or pore formers, homogenizing this mixture and shaping it to the desired shaped bodies, calcining the shaped body and activating the catalytic precursor thus obtained by partly or completely leaching-out the leachable alloy component and, if appropriate, finally washing the finished catalyst.

A further specific embodiment of catalysts which are suitable particularly advantageously for use in the process according to the invention is that of catalysts which comprise copper in oxidic form and if appropriate additionally in elemental form. The hydrogenation catalyst used in step b) then preferably comprises at least 23% by weight, more preferably at least 35% by weight, of copper in oxidic and/or elemental form, based on the total weight of the catalyst.

A frequently employed process for preparing such catalysts consists in the impregnation of support materials with solutions of the catalyst components, which are subsequently converted to the catalytically active state by thermal treatment, decomposition or reduction.

A further suitable process for preparing catalysts comprises the precipitation of one catalyst component or the coprecipitation of two or more than two catalyst components. For instance, a shaped catalyst body can be prepared by precipitating a copper compound, if appropriate, at least one further metal compound and/or an additive, and then subjecting it to drying, calcining and shaping. The precipitation can be carried out in the presence of a support material. Suitable starting materials for the precipitation are metal salts and metal complexes. The copper compounds used for the precipitation may in principle be all known Cu(I) and/or Cu(II) salts which are soluble in the solvents used for application to the support. These include, for example, nitrates, carbonates, acetates, oxalates or ammonium complexes. In a preferred embodiment, copper nitrate is used. The catalytically active component of the catalyst may, apart from a copper compound, comprise further elements as additives, for example, metals, nonmetals and compounds thereof. These are preferably metals of groups 4 to 15 and the lanthanides. Particularly preferred metals are La, Ti, Zr, Cu, Mo, W, Mn, Re, Co, Ni, Cu, Ag, Au, Zn, Sn, Pb, As, Sb and Bi. Preference is given to using an aqueous medium for the precipitation.

Suitable aqueous media are substances or mixtures which are liquid under the process conditions and which comprise at least 10% by weight, more preferably at least 30% by weight, especially at least 50% by weight, of water. The proportion other than water is preferably selected from inorganic or organic compounds which are at least partly soluble in water or at least partly miscible with water. For example, the compounds other than water are selected from organic solvents such as $C_1$-$C_{20}$ alkanols, especially methanol, ethanol, n-propanol, isopropanol, n-butanol, sec-butanol, tert-butanol, pentanols and hexanols, $C_4$-$C_8$ cycloalkyl ethers, such as tetrahydrofurans, pyrans, dioxanes and trioxanes, $C_1$-$C_{12}$ dialkyl ethers, such as dimethyl ether, dibutyl ether and methyl butyl ether. The aqueous medium preferably comprises less than 40% by weight, more preferably less than 30% by weight and especially less than 20% by weight of organic solvent. In a preferred embodiment of the process according to the invention, the aqueous medium is essentially free of organic solvents.

The precipitation can be induced by known processes, for example, cooling of a saturated solution, addition of a precipitant, etc. Suitable precipitants are, for example, acids, bases, reducing agents, etc.

The precipitation can be induced by adding an acid or a base to the aqueous medium which comprises the copper compound and, if appropriate, further compounds. Suitable acids are mineral acids, such as HCl, $H_2SO_4$ and $H_3PO_4$. The base is preferably selected from metal oxides, metal hydroxides, especially alkali metal hydroxides, such as sodium hydroxide and potassium hydroxide, metal carbonates, especially alkali metal and alkaline earth metal carbonates, such as lithium carbonate, sodium carbonate, potassium carbonate, magnesium carbonate, and calcium carbonate, nitrogen bases, especially ammonia and primary, secondary and tertiary amines.

Examples of suitable reducing agents are carboxylic acids, such as formic acid, citric acid, lactic acid, tartaric acid, and especially salts of carboxylic acids, preferably the alkali metal, alkaline earth metal, ammonium and $C_1$-$C_{10}$ alkyl ammonium salts, phosphorous or hypophosphorous acid, the salts of phosphorous or hypophosphorous acid, especially the alkali metal or alkaline earth metal salts, $C_1$-$C_{10}$ alkanols, such as methanol, ethanol and isopropanol, sugars, such as aldoses and ketoses in the form of monosaccharides, disaccharides and oligosaccharides, especially glucose, fructose and lactose, aldehydes, such as formaldehyde, boron-hydrogen compounds such as boron hydrides, boranes, metal boranates and borane complexes such as diborane, sodium borohydride and aminoboranes, especially trimethylaminoborane, hydrazine and alkylhydrazines, such as methylhydrazine, hydrogendithionites and dithionites, especially sodium and potassium hydrogendithionite, sodium, potassium and zinc dithionites, hydrogensulfides and sulfides, especially sodium and potassium hydrogensulfides, sodium, potassium and calcium sulfides, hydroxylamine and urea and mixtures thereof.

Suitable catalysts for the hydrogenation are, for example, those which comprise, on a support composed of silica, nickel and copper as well as other metals as active constituents. Such catalysts are described, for example, in DE-A 26 28 987. The active composition of these catalysts comprises especially from 40 to 80% by weight of nickel, from 10 to 50% by weight of copper and from 2 to 10% by weight of manganese.

EP-A-0 434 062 describes hydrogenation catalysts which are obtainable by reducing a precursor composed of oxides of copper, of aluminum and of at least one further metal selected from magnesium, zinc, titanium, zirconium, tin, nickel and cobalt.

Suitable hydrogenation catalysts are also those described in DE 102 18 849, which comprise from 0.1 to 10% by weight of chromium, calculated as $Cr_2O_3$, from 0.1 to 10% by weight of calcium, calculated as $CaO_x$ and from 5 to 20% by weight of copper, calculated as CuO, deposited on a silicon dioxide support material and based in each case on the total weight of the calcined catalyst.

DE-A-40 21 230 discloses copper zirconium oxide catalysts wherein the ratio of copper atoms to zirconium atoms, expressed as the weight ratio, is from 1:9 to 9:1.

DE-A-4 028 295 describes copper-manganese hydrogenation catalysts.

EP-A-552463 describes, in a first embodiment, hydrogenation catalysts for which the oxidic form corresponds essentially to the composition $Cu_aAl_bZr_cMn_dO_x$, where the following relationships apply: a>0; b>0; c≧0; d>0; a>b/2; b>a/4; a>c; a>d; and x denotes the number of oxygen ions required per formula unit to ensure electrical neutrality. In a further embodiment, the inventive catalyst comprises a smaller proportion of aluminum oxide. The catalyst in this embodiment corresponds essentially to the composition $Cu_aAl_bZr_cMn_dO_x$, where the following relationships apply: a>0; a/4≧b≧a/40; c≧0; d>0; a>c; 0.95d≧a≧0.5d and x denotes the number of oxygen ions required per formula unit to ensure electrical neutrality.

WO 2006/005505 describes shaped catalyst bodies which are particularly suitable for use in the process according to the invention. These may be prepared by a process in which
(i) an oxidic material comprising copper oxide, aluminum oxide and at least one of the oxides of lanthanum, tungsten, molybdenum, titanium or zirconium, with preference being given to the oxides of lanthanum and/or tungsten, is made available,
(ii) pulverulent metallic copper, copper flakes, pulverulent cement or mixtures thereof or a mixture thereof with graphite can be added to the oxidic material, and
(iii) the mixture resulting from (ii) is shaped to form a catalyst pellet or a catalyst extrudate having a diameter d and/or a height h of <6.0 mm, catalyst spheres having a diameter d of <6.0 mm or catalyst honeycombs having a cell diameter $r_z$ of <6.0 mm.

Among the oxides of lanthanum, tungsten, molybdenum, titanium or zirconium, lanthanum oxide is preferred. The composition of the oxidic material is generally such that the proportion of copper oxide is in the range from 40 to 90% by weight, the proportion of oxides of lanthanum, tungsten, molybdenum, titanium or zirconium is in the range from 0 to 50% by weight and the proportion of aluminum oxide is up to 50% by weight, in each case based on the total weight of the sum of the above-mentioned oxidic constituents, with these three oxides together making up at least 80% by weight of the oxidic material after calcination and cement not being included as part of the oxidic material in the above sense.

In a preferred embodiment, the oxidic material comprises
(a) copper oxide in a proportion in the range 50≦x≦80% by weight, preferably 55≦x≦75% by weight,
(b) aluminum oxide in a proportion in the range 15≦y≦35% by weight, preferably 20≦y≦30% by weight, and
(c) at least one of the oxides of lanthanum, tungsten, molybdenum, titanium or zirconium, preferably of lanthanum and/or tungsten, in a proportion in the range 2≦z≦20% by weight, preferably 3≦z≦15% by weight,
in each case based on the total weight of the oxidic material after calcination, where 80≦x+y+z≦100, in particular 95≦x+y+z≦100.

Preferred catalysts comprise the following metals in oxidic form, reduced form (elemental form) or a combination thereof. Metals which are stable in more than one oxidation state can be used completely in one of the oxidation states or in different oxidation states:

Cu
Cu, Ti
Cu, Zr
Cu, Mn
Cu, Al
Cu, Ni, Mn
Cu, Al, at least one further metal selected from La, W, Mo, Mn, Zn, Ti, Zr, Sn, Ni, Co
Cu, Zn, Zr
Cu, Cr, Ca
Cu, Cr, C
Cu, Al, Mn, if appropriate Zr.

Particularly preferred catalysts comprise the following metals:

Cu
Cu, Ti
Cu, Al
Cu, Al, La
Cu, Al, Zn
Cu, Zn, Zr
Cu, Al, Mn
Cu, Cr, C.

The inert support material used for the inventive catalysts may be virtually any prior art support materials, as find use advantageously in the preparation of supported catalysts, for example, $SiO_2$ (quartz), porcelain, magnesium oxide, tin dioxide, silicon carbide, $TiO_2$ (rutile, anatase), $Al_2O_3$ (alumina), aluminum silicate, steatite (magnesium silicate), zirconium silicate, cerium silicate or mixtures of these support materials. Preferred support materials are aluminum oxide and silicon dioxide. The silicon dioxide support material used for catalyst preparation may be silicon dioxide materials of different origin and preparation, for example, fumed silicas, or silicas prepared by wet chemical means, such as silica gels, aerogels, or precipitated silicas (for preparation of the different $SiO_2$ starting materials see: W. Büchner; R. Schliebs; G. Winter; K. H. Michel: Industrielle Anorganische Chemie [Industrial Inorganic Chemistry]; 2nd ed., p. 532-533, VCH Verlagsgesellschaft, Weinheim 1986).

The catalysts may be used as shaped bodies, for example in the form of spheres, rings, cylinders, cubes, cuboids or other geometric bodies. Unsupported catalysts can be shaped by customary processes, for example by extrusion, tableting, etc. The shape of supported catalysts is determined by the shape of the support. Alternatively, the support can be subjected to a shaping process before or after the application of the catalytically active component(s). The catalysts may, for example, be used in the form of pressed cylinders, tablets, pellets, wagonwheels, rings, stars or extrudates, such as solid extrudates, polylobal extrudates, hollow extrudates and honeycombs or other geometric bodies.

The catalyst particles generally have a mean of the (greatest) diameter of from 0.5 to 20 mm, preferably from 1 to 10 mm. This includes, for example, catalysts in the form of tablets, for example with a diameter of from 1 to 7 mm, preferably from 2 to 6 mm, and a height of from 3 to 5 mm, rings with, for example, external diameter from 4 to 7 mm, preferably from 5 to 7 mm, height from 2 to 5 mm and hole diameter from 2 to 3 mm, or extrudates of different length of diameter of, for example, from 1.0 to 5 mm. Such shapes can be obtained in a manner known per se by tableting or extrusion. To this end, customary assistants, for example lubricants such as graphite, polyethylene oxide, cellulose or fatty acids (such as stearic acid), and/or shaping assistants and reinforcers such as fibers of glass, asbestos or silicon carbide, may be added to the catalyst composition.

A specific embodiment of supported catalysts is that of coated catalysts. Coated catalysts are preferably also suitable for the process according to the invention. Coated catalysts comprise a catalytic composition applied in coating form to a support. They may be present in the form of spheres, rings, cylinders, cubes, cuboids, or other geometric shapes. Irrespective of the type and composition of the catalytically active material, coated catalyst particles can in principle be provided by contacting the support with a liquid binder and the catalytically active composition, applying a layer of the composition to the support and then, if appropriate, partly removing the binder. To provide the catalyst particles, the catalytically active material is applied actually in its finished catalytically active form, for example as a calcined mixed oxide. Suitable processes for preparing coated catalysts are described, for example, in DE-A-29 09 671 and in EP-A-714 700. According to the latter process, the support is first moistened with the liquid binder, then a layer of active catalyst composition is adhered on the surface of the moistened support body by contacting with dry, finely divided, active catalyst composition, and then the liquid binder is partly removed if appropriate. In a specific embodiment, the steps of moistening the support, of contacting with the catalyst composition and of removing the liquid binder are repeated once or more than once until the desired layer thickness of the coated catalyst has been attained.

A further specific embodiment of supported catalysts is that of catalysts prepared by impregnation processes. To this end, the catalytically active catalyst components or precursor compounds thereof can be applied to the support material. In general, the support material is impregnated by applying aqueous salt solutions of the components, for example, aqueous solutions of their halides, sulfates, nitrates, etc. The copper component may, for example, also be applied to the support material in the form of an aqueous solution of its amine complex salts, for example as a [Cu(NH$_3$)$_4$]SO$_4$ or as a [Cu(NH$_3$)$_4$](NO$_3$)$_2$ solution, if appropriate in the presence of sodium carbonate. It will be appreciated that it is also possible to use copper-amine complexes other than those mentioned by way of example for the catalyst preparation with the same success.

The support material in principle can be impregnated with the precursor compounds of the catalytically active components in one stage or a plurality of stages. The impregnation can be undertaken in conventional impregnation apparatus, for example impregnating drums. After drying and/or calcination, the finished catalyst is then obtained. The impregnated shaped catalyst bodies can be dried continuously or batchwise, for example in a belt or tray oven. The drying can be effected at atmospheric pressure or reduced pressure. In addition, the drying can be effected in a gas stream, for example, an air stream or a nitrogen stream. According to the pressure employed, the drying is performed generally at temperatures of from 50 to 200° C., preferably from 80 to 150° C. The catalyst which may have been dried beforehand is calcined generally at temperatures of from 200 to 800° C., preferably from 500 to 700° C. The calcination can, like the drying, be performed continuously or batchwise, for example, in a belt or tray oven. The calcination can be effected under atmospheric pressure or reduced pressure and/or in a gas stream, for example in an air stream or a hydrogen stream. A pretreatment with hydrogen or hydrogen-comprising gases, generally under conditions which correspond to the hydrogenation conditions, serves to pre-reduce/activate the hydrogenation catalyst. The catalyst may, though, also be reduced in situ under the conditions established in the hydrogenation, preferably under pressure (for example at a hydrogen pressure of from about 100 to 325 bar).

The hydrogenation discharge consists essentially of 1,2-propanediol. Further constituents include methanol, ethanol, n-propanol, isopropanol, 1,3-propanediol, glycerol, ethylene glycol and water. The hydrogenation discharge can subsequently be worked up by customary processes known to those skilled in the art. Suitable examples are thermal processes, preferably distillation processes, adsorption, ion exchange, membrane separation processes, crystallization, extraction or a combination of two or more of these processes. The hydrogenation discharge is preferably worked up by distillation. For this purpose, suitable distillation processes are customary distillation processes known to those skilled in the art. Suitable apparatus for the distillative workup comprises distillation columns such as tray columns, which may be provided with bubble-caps, sieve plates, sieve trays, structured packings, internals, valves, side draws, etc. Especially suitable are dividing wall columns, which may be provided with side draws, recycle lines, etc. For distillation, it is possible to use a combination of two or more than two distillation columns. Also suitable are evaporators, such as thin-film evaporators, falling-film evaporators, Sambay evaporators, etc. and combinations thereof. Glycerol still present in the hydrogenation discharge may, if appropriate after distillative removal, be recycled into the hydrogenation stage.

The invention is illustrated in detail, with reference to the following non-restrictive examples.

EXAMPLES

FIG. 1 shows the diagram of the two-stage reactor cascade used to perform the hydrogenation process according to example 1, omitting those details which are not relevant for the explanation of the invention for reasons of clarity.

Example 1

The reactor (1) used is a shaft reactor having a catalyst volume of 540 l. This comprises, installed as a catalyst, an oxidic material which comprises $CuO_{0.6-0.85}(Al_2O_3)_{0.1-0.34}(La_2O_3)_{0.01-0.2}$ and which, based on the total weight of the oxidic material, may comprise up to 20% auxiliaries. The catalyst is reduced in the hydrogen stream before the hydrogenation reaction. The postreactor (8) formed without a circulation stream has a catalyst volume of 120 l and comprises the same catalyst as the main reactor (1).

As the feed stream (3), pure glycerol is mixed with water in a mass ratio of glycerol to water of 9:1. The feed stream (3) (approx. 110 kg/h) is brought to reaction pressure with a pump (not shown) and, together with the recycle stream (7), conducted to the reactor at a temperature of 175° C.

The reaction to give 1,2-propanediol is performed in reactor (1) at a pressure of 200 bar. For this purpose, under pressure control, hydrogen is fed via line (2) to reactor (1). The amount of hydrogen which is added to the reactor is calculated from the consumption in the reaction and the amount of offgas (stoichiometric excess of hydrogen from 10 mol % to 25 mol %). Reactor (1) is flowed through from the top downward in cocurrent. The conversion in the main reactor is from approx. 93 to 94%. The biphasic reactor discharge (4) is separated in the separator (10) into a gas-rich phase and a liquid phase. The liquid phase is first fed to the heat exchanger (6) for cooling by means of pump (5) as a circulation stream. The temperature of the recycle stream in the heat exchanger (6) is adjusted such that an inlet temperature of 175° C. is achieved at the top of the reactor with the mixing of the feed stream (3). The recycle ratio (recycle stream (7) to feed stream (3)) is approx. 13. The reactor (1) is cooled sufficiently by the cycle stream and the cold glycerol-containing feed (3) supplied. The second substream withdrawn from the separator (10) is cooled to the inlet temperature of the postreactor of approx. 175° C. in a further cooler (not shown). The cooled biphasic stream is fed to the top of the postreactor (8). In the reactor (8), the hydrogenation is continued up to a total conversion of approx. 99%.

The invention claimed is:

1. A process for preparing 1,2-propanediol comprising
   a) proving a glycerol-containing stream, and
   b) subjecting the glycerol-containing stream to a continuous hydrogenation in two hydrogenation reactors connected in series in the presence of a heterogeneous copper catalyst, the conversion in the first reactor being at least 80%, based on the glycerol content, and the continuous hydrogenation in both hydrogenation reactors being effected at a pressure in the range from 30 to 300 bar.

2. The process according to claim 1, wherein the continuous hydrogenation in both hydrogenation reactors is effected at a temperature in the range from 150 to 250° C.

3. The process according to claim 1, wherein the continuous hydrogenation in both hydrogenation reactors is effected at a pressure in the range from 60 to 250 bar.

4. The process according to claim 1, wherein the total glycerol conversion in step b), based on the glycerol present in the glycerol-containing stream, is at least 97%.

5. The process according to claim 1, wherein the total glycerol conversion in step b), based on the glycerol present in the glycerol-containing stream, is at least 99%.

6. The process according to claim 1, wherein two fixed bed reactors connected in series are used for the continuous hydrogenation in step b).

7. The process according to claim 1, wherein the reaction is performed adiabatically in the second reactor.

8. The process according to claim 1, wherein the second reactor is operated in straight pass.

9. The process according to claim 1, wherein hydrogen is fed only into the first reactor.

10. The process according to claim 1, in which a glycerol-containing stream which is obtained in the preparation of alkyl esters of higher fatty acids by transesterification of fatty acid triglycerides is provided in step a).

11. The process according to claim 1, wherein the glycerol-containing stream has a water content of at most 30% by weight.

12. The process according to claim 1, wherein the glycerol-containing stream has a water content of at most 20% by weight.

13. The process according to claim 1, wherein the glycerol-containing stream is essentially anhydrous.

14. The process according to claim 1, in which the glycerol-containing stream is subjected in step a) to a workup by at least one workup process which is selected from thermal workup, adsorption, ion exchange, membrane separation, crystallization, extraction or a combination of two or more of these processes.

15. The process according to claim 1, in which the glycerol-containing stream is subjected in step a) to a distillation to reduce the water content and/or to remove components which impair the catalytic hydrogenation.

16. The process according to claim 1, in which the glycerol-containing stream is subjected in step a) to a catalytic desulfurization, optionally in the presence of hydrogen, to reduce the content of sulfur compounds.

17. The process according to claim 1, in which the glycerol-containing stream is subjected in step a) to a catalytic desulfurization, optionally in the presence of hydrogen, to reduce the content of aromatic sulfur compounds.

18. The process according to claim 1, in which the glycerol-containing stream is contacted in step a) with at least one adsorbent to remove components which impair the catalytic hydrogenation.

19. The process according to claim 18, wherein the adsorbent comprises at least one component capable of being used as a hydrogenation catalyst in step b).

20. The process according to claim 1, wherein the provision of the glycerol-containing stream in step a) comprises the following steps:
   a1) providing a biogenic fat- and/or oil-containing starting mixture,
   a2) transesterifying the fatty acid triglycerides present in the starting mixture with at least one $C_1$-$C_9$ monoalcohol and optionally esterifying the free fatty acids present in the starting mixture to form an esterification mixture,
   a3) separating the esterification mixture to obtain at least one fraction enriched in $C_1$-$C_9$ monoalkyl esters and at least one fraction enriched in glycerol released in the transesterification,
   a4) optionally, purifying the glycerol-enriched fraction.

* * * * *